United States Patent [19]

Graham et al.

[11] 3,992,528

[45] Nov. 16, 1976

[54] ANTI-VIRAL SUBSTANCE CONTAINING PEPTIDE, FATTY ACID AND CARBOHYDRATE MOIETIES

[75] Inventors: Shirl O. Graham; Sarangamat Gurusiddaiah, both of Pullman, Wash.

[73] Assignee: Research Corporation, New York, N.Y.

[22] Filed: Feb. 18, 1975

[21] Appl. No.: 550,745

[52] U.S. Cl. .......................... 424/177; 260/112 R; 195/80 R
[51] Int. Cl.² ................. A61K 37/00; C07C 103/52
[58] Field of Search ............... 260/112 R, 112.5 R; 195/80 R; 424/177, 118, 119, 120, 121, 122

[56] References Cited
UNITED STATES PATENTS

| | | |
|---|---|---|
| 3,018,220 | 1/1962 | McGuire et al. ................. 195/80 R |
| 3,032,470 | 5/1962 | Ziffer et al. ........................ 424/118 |
| 3,344,024 | 9/1967 | Whaley et al. ..................... 195/80 R |
| 3,495,004 | 2/1970 | Voe et al. .......................... 195/80 R |
| 3,629,404 | 12/1971 | Florent et al. ..................... 195/80 R |
| 3,856,939 | 12/1974 | Ellestad et al. ................... 195/80 R |

*Primary Examiner*—Lewis Gotts
*Assistant Examiner*—Reginald J. Suyat
*Attorney, Agent, or Firm*—Cooper, Dunham, Clark, Griffin & Moran

[57] ABSTRACT

Antimicrobial agent particularly effective as an antiviral agent but also exhibiting antifungal and antibacterial activity characterized as a triad containing peptide, fatty acid and carbohydrate moieties.

7 Claims, 1 Drawing Figure

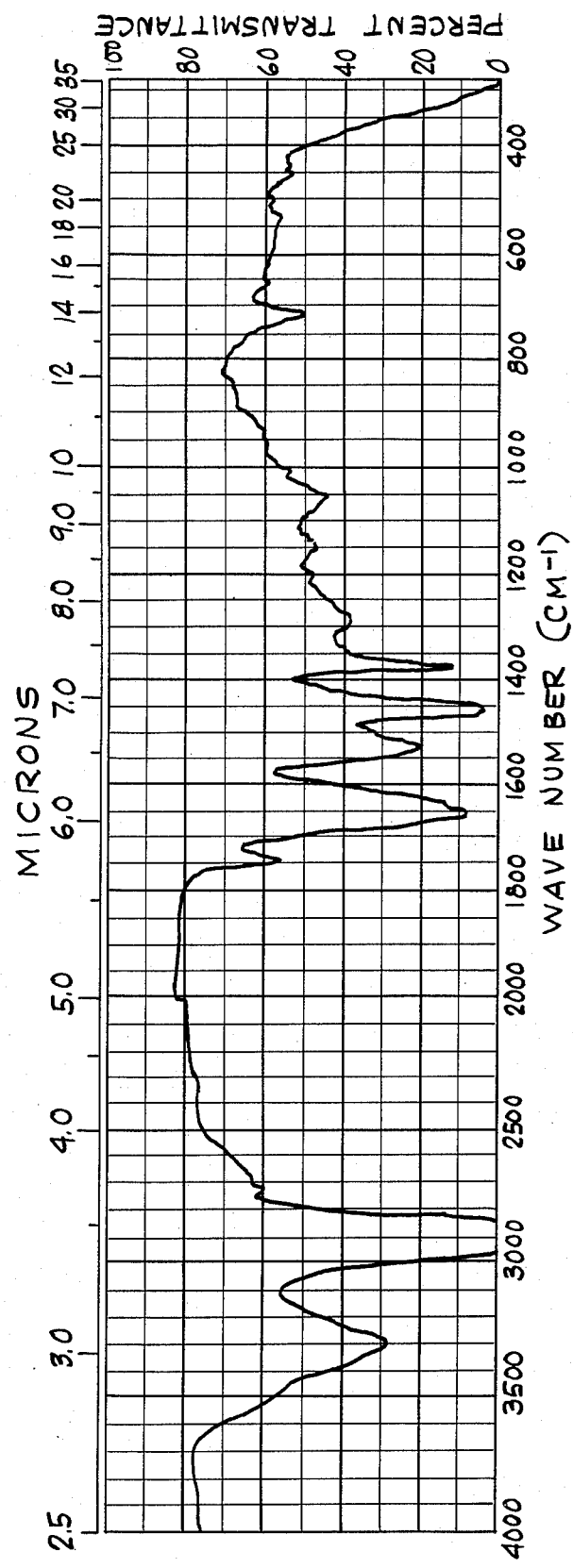

ANTI-VIRAL SUBSTANCE CONTAINING PEPTIDE, FATTY ACID AND CARBOHYDRATE MOIETIES

This invention relates to a novel material useful in the treatment of viral, fungal or microbial infections of plants and mammals. For convenience, this material will be referred to herein as an antimicrobial agent.

The antimicrobial agent of this invention is a triad characterized as containing a peptide, a fatty acid and a carbohydrate moiety. While it is especially effective in the control of viral infections, it also manifests activity against fungi and bacteria. The results of amino acid analysis indicate that the peptide contains the following amino acids in the mole ratios indicated:

| | |
|---|---|
| d-threonine (2) | l-serine (1) |
| d-alanine (2) | l-proline (1) |
| alloisoleucine (1.9) | glycine (1) |
| d-valine (1.8) | l-dehydrobutyrin (1) |
| l-valine (1.8) | N-methyl threonine (1) |

It also contains 1-leucine and 1-isoleucine in the combined mole ratio 0.1 based on the other amino acids, and one other basic amino acid which presently appears to be a cyclic form of arginine.

The fatty acid moiety is isolable as a hydrolysis product from the treatment of the antimicrobial agent for 24 hours with 6N hydrochloric acid. Mass spectrometric analysis indicates that the principal fatty acid is an analog of myristic acid which is unsaturated between carbon atoms 6 and 7 and is present in about 60% by weight. The moiety also contains about 27% iso-tridecanoic acid, about 8% lauric acid, and about 5% undecanoic acid.

The presence of the carbohydrate moiety is established by hydrolysis with 2N sulfuric acid for 6 hours at 94° C in sealed ampule. After neutralization with barium hydroxide and filtration, the filtrate gives a positive Molisch reaction and also gives and orange color with a 1:5 mixture of phenol and concentrated sulfuric acids. It tests negative, however, when assessed for pentose or hexose sugars or sugar amines.

Products obtained during hydrolysis including those from which all carbohydrate has not been completely removed have antimicrobial utility.

The antimicrobial agent of this invention is obtained as a fermentation product from the cultivation of *Streptomyces hygroscopicus* NRRL 2751. A morphological description of this organism is given in U.S. Pat. No. 3,032,470 which describes the preparation of the antifungal antibiotic phytostreptin. The products of this invention, however, do not have the same physical and chemical properties as phytostreptin and are clearly different materials. For example, phytostreptin is not soluble in methyl ethyl ketone whereas the antimicrobial agent of this invention is soluble in this reagent. Phytostreptin is soluble in water whereas the antimicrobial agent of this invention is not soluble in water. Additionally, the infrared curve of the antimicrobial agent of this invention is markedly different from that of phytostreptin as will be apparent from a comparison of FIG. 1 herein and the infrared curve for phytostreptin shown as FIG. 3 of the above identified patent. The principal maxima of the products are as follows:

| Antiviral (KBr) (in microns) | Phytostreptin (Chloroform) (in microns) |
|---|---|
| 2.85 | 2.93 |
| 2.90 | 3.08 |
| 2.95 | 3.20 |
| 2.99 | 3.33 |
| 3.10 | 3.45 |
| 3.15 | 3.52 |
| 3.25 | 4.12 |
| 3.45 | 5.71 |
| 3.60 | 5.74 |
| 4.25 | 6.05 |
| 6.00 | 6.15 |
| 6.20 | 6.56 |
| 6.50 | 6.70 |
| 6.90 | 6.95 |
| 7.15 | 7.12 |
| 7.70 | 7.60 |
| 7.81 | 7.76 |
| 7.95 | 7.86 |
| 8.85 | 8.12 |
| 8.90 | 8.86 |
| 14.00 | 9.05 |
| | 9.42 |
| | 10.06 |
| | 10.34 |
| | 10.80 |
| | 11.00 |
| | 11.46 |
| | 11.70 |
| | 13.30 |

The antimicrobial agent is produced and recovered from a culture medium fermented by *S. hygroscopicus* NRRL 2751 as follows:

I. Culture media and conditions
   A. Seed culture medium (Liter basis)

| | |
|---|---|
| Yeast Extract | 5 gm |
| Corn Steep Liquor | 10 ml |
| Glucose | 20 gm |
| Water | 1 L |

Adjust to pH 6.5 and add 1.5 gm CaCO$_3$.
Sterilize 20 min at 15 lbs. pressure.
Inoculate 300 ml of seed medium in a 500 ml Erlenmeyer flask with culture of *S. hygroscopicus* strain 2751 and incubate at 25° C for 6 days on a rotary shaker with moderate agitation.
Use entire culture as inoculum for one 10 L fermentation.

B. Fermentation medium (10 Liter ferment)

| | |
|---|---|
| Soy Hydrolysate | 300 gm |
| Corn Steep Liquor | 100 ml |
| Glucose | 100 gm |
| Yeast Extract | 50 gm |
| Water | 10 L |

Adjust to pH 6.5 and add 15 gm CaCO$_3$.
Sterilize 20 min. at 15 lbs. pressure.
Add seed culture to medium in a 10 L fermenter and incubate at 27° C for 5 days with 1.5 L/min. sterile air bubbled into medium and agitator set at 300 rpm.
It has been observed that maximim production of the antimicrobial agent occurs by the sixth day. However, since lysis starts to occur on the fifth day, it is preferred to recover the agent from the cells on the fifth day. While this may incur some loss of product, it is presently considered to be the most efficient procedure since there are fewer impurities to deal with in the cells than in the fermented culture medium.

II. Isolation and purification of the antimicrobial agent from cultural ferments 1. Remove cells from ferment by centrifugation (± 500 gm fresh weight/10 L ferment).
2. Grind to rupture cells under isopropanol using fine glass beads.
3. Filter off cell debris and glass beads and take isopropanol extract to dryness.
4. Extract residue with petroleum ether to remove lipids and pigments and discard extract.
5. Extract residue with methyl-ethyl-ketone (MEK) to dissolve antimicrobial agent. Concentrate to small volume.
6. Precipitate antimicrobial agent preferentially from MEK concentrate by adding dropwise to swirling chilled petroleum ether (ratio 1:20; conc: Pet ETO) over a 30 min. period.
7. Collect precipitate on celite-layered sintered glass filter and rinse with petroleum ether.
8. Wash precipitate on the filter cake with deionized, glass-distilled water to remove water soluble peptides and antibiotic impurities. Dry filter cake in situ.
9. Extract antimicrobial agent from filter cake with ethylene dichloride and concentrate the extract to 1/10 volume.
10. Add ethylene dichloride concentrate dropwise into chilled petroleum ether (ratio 1:10) to precipitate antimicrobial agent.
11. Collect antimicrobial agent on a celite layered sintered glass filter. Evaporate residual solvent from cake.
12. Extract antimicrobial agent from filter cake with 95% ethanol and reduce to very small volume.
13. Layer ethanolic extract on top of an LH-20 Sephadex gel column (0.9 ± 24.5 cm bed) and elute highly purified antimicrobial agent preferentially with 50% ethanol in deionized, glass distilled water, using a 10 ml/hr flow rate (antimicrobial agent elutes in 1 hr. 20 min.).
14. Take eluate to dryness.

The fermentation process of this invention may be generally described as an aerobic fermentation in a fermentation medium containing a source of carbon and nitrogen. The isolation and purification procedure is essentially an extraction, adsorption and elution procedure. It is important, however, that the procedural steps outlined above be followed without substantial variation so as to insure maximum production of the desired antimicrobial agent.

It has been observed that S. hygroscopicus NRRL 2751 is extremely temperature sensitive. In order to obtain the optimum yield of purified product following the procedure set forth above, it is important that the following observations be kept in mind.

The donor organism should not be stored or maintained for long periods on a rich cultural medium, since mutants arise that fail to produce antimicrobial agent or produce minimal levels of it. The organism readily stores unchanged for 12 months or longer at room temperatures in sterile physiologic saline. This is an appropriate source for seed inoculum. The organism remains viable and unchanged as well for 12 months or longer in sterile distilled water. In either of these solutions the organism may be stored at refrigerated temperatures no lower than 15° C. Below 15° C cells are killed during extensive storage. The organism remains viable and unchanged at ambient room temperatures for 24 months or longer when placed in sterile, fine sandy loam soil allowed to dry to ±4% moisture (by wt.). The organism is morphologically and physiologically altered in culture by exposure to temperatures below 10° C, and seed cultures should not be initiated from such sources. Barren versus productive cultures for seed media initiation are recognizable by their growth habits on suitable agar media such as potato dextrose agar, actinomycete broth agar, or nutrient broth agar. Barren cultures exhibit a mounded growth habit of a tannish-mauve color on these media. Productive cultures are resupinate, initially white in colony color, changing on the outer surface to a salt and pepper to a charcoal color with a crusted appearance as propagules are produced. Cultures of the resupinate kind should be used as a source of the donor organism in preparation of seed cultures. The donor organism can be perpetuated by lyophilization and stored in vacuum sealed ampules. However, because the organism is frozen before it is sublimed, the perpetuated thalli and propagules give rise, initially only to barren cultures. Sectoring into resupinate growth habit develops erratically in time and subcultures made from these kinds of sectors reclaim biotypes of productive character.

The chemical constituents of the antimicrobial agent and chemical properties which may be useful for identification are set forth below:

I. Tests for homogeneity
  a. By thin layer chromatography
    Support: silica gel G with phosphor and binder on glass plates
    Solvent: n-Butanol-acetic acid-water, ratio 3:1:1 (V:V:V). The antiviral invention migrates as a single compact spot with an $R^f$ of 0.52.
  b. By electrophoresis
    1. Disc. electrophoresis: (Method of Brewer and Ashworth. Journal of Chem. Ed. 46: 41–45. 1969)
    Support: 7.5% acrylamide lower gel, pH 8.9 2.5% acrylamide upper gel, pH 6.9
    Buffer: TRIS-Glycine, pH 8.3
    Tube diam: 0.5 cm (I.D) x 6 cm L
    Current: 1.5/m A per tube
    Length of run: 3 hours
    Tracking dye: 0.001% Bromophenol Blue in $H_2O$
    The $R_f$ value ($=R^{tracking\ dye}$) was 0.63 for the antiviral invention, and no secondary or minor bands were resolved.
  c. By analytical ultracentrifugation
    Instrument: Beckman Model E Analytical Ultracentrifuge
    System: Schlieren
    Sample: 6 mg/ml in $H_2O$
    Temperature: 20° C
    Rotor: An D
    Speed: 52,000 rpm
    Length of run: 4 hours
    The antimicrobial agent migrated as a single symmetrical peak throughout the run and the $S_{20}W$ value was calculated at 1.73.

II. Tests for composition
  a. Intact antimicrobial agent (10 $\mu$ samples)
    1. Molisch test—positive (purple-brown color)
    2. Ninhydrin test—positive
    3. Biuret test—positive
    4. Anthrone test—negative 5. Phenol-$H_2SO_4$ (Dubois method)—positive
6. Carbazole test—weakly positive
7. Taubers test'negative
8. Benzidine—glacial acetic acid test for pentose—negative
9. Bials test—negative
10. Moores test—negative
11. Liebermann—Burchard test —negative III. Physical characterizations of the antiviral invention a. Molecular weight By differential refractometry and light scattering the molecular weight of the antimicrobial agent appears to be 14,000 ± 200.

b. Infrared Spectrophotometry

The antimicrobial agent dispersed in Nujol shows a number of characteristic absorption bands in the infrared region, utilizing a Hitachi-Perkin Elmer Infrared Spectrophotometer, as will be apparent from FIG. 1, and from the previous listing of principal maxima.

c. Ultraviolet absorption spectrum the antimicrobial agent (100 mg/ml in spectral grade methanol) exhibits strong end absorption in the lower regions of the UV spectrum. There are no maxima in the entire region 230–410 mn. Determinations were made on a Beckman double-beam spectrophotometer.

d. Fluorescence spectrophotometry

The antimicrobial agent (12.5 $\mu$gm/ml) dissolved in double distilled water was assessed in a Hitachi MPF2A fluorescence spectrophotometer. Excitation occurs at 380 m$\mu$; excitation occurs as a background peak with a sharp scatter peak occurring at 445 m$\mu$, emission occurs as a broad peak with a sharp scatter peak occurring at 395 m$\mu$.

e. Elemental analysis of the antiviral invention gave the following average percentage values

| C | H | N |
|---|---|---|
| 54.82 | 8.04 | 12.99 | f. Chromatographic migration (TLC)

| System | Support | | Rf |
|---|---|---|---|
| n-Butanol-acetic acid-water (3:1:1) (V:V:V) | a. | Silica gel G w/ phosphor & binder | .52 |
| | b. | Eastman Chromogram sheets without fluorescent indicator | .69 |

For the isolation and identification of the fatty acid moiety, the purified antimicrobial agent was hydrolyzed for 24 hours in 6N hydrochloric acid. The hydrolysate was diluted with 15 ml double distilled water and mixed with 20 ml of diethyl ether in a separatory funnel. The ether layer was drawn off and the aqueous phase was extracted two more times with fresh diethyl ether. The ether phases were combined and evaporated to dryness. The residue was redissolved in chloroform and spotted to TLC plates coated with silica gel G plus phosphor and binder. Using as a solvent anhydrous ether-hexane-formic acid (80:20:2; V:V:V) the chromatograms were developed by thin layer chromatography, dried and viewed under UV to define spots. Spots were scraped from the TLC plates and extracted with chloroform-methanol solution (2:1; V/V) to elute fatty acids. The solvent was evaporated from the acids and the free fatty acid residues were converted to their esters by $BF_3$ in methanol under reflux in a steam bath for 30 minutes. Double distilled water was added to the reflux mixture to stop the reaction and the extract was washed with chloroform 3 times to partition the fatty acid esters. The chloroform extract was evaporated to dryness and the residue was assessed by standard procedures of gas chromatography and mass spectrometry. The fatty acids and the relative amounts thereof have been described above.

The efficacy of the antimicrobial agent of the invention as an antiviral agent was shown by a tissue culture test against Newcastle Disease Virus (NDV) utilizing chick embryo fibroblasts, specifically Sp. No. 4423 NDV (Blacksburg strain) using the modified egg-bit technique of Beard (Avian Diseases 13: 309 (1969). In accordance with this test, 0.5 ml of a 1 mg/ml concentration of the antimicrobial agent and 0.5 ml of Newcastles Disease Virus (NDV) Sp. No. 4423 diluted $10^{-2}$ were thoroughly mixed with 4.0 ml of egg-bit tissue culture medium. A control was prepared, consisting of 4.5 ml egg-bit medium thoroughly mixed with 0.5 ml of the NDV culture. Treatments were incubated for 50 min. at room temperature. At the end of the incubation period, both treatments were titrated by decimal dilutions. One drop of each dilution was added to each of five egg-bit culture wells containing a chorioallantoic membrane egg-bit in 0.5 ml of tissue culture medium. Cultures were incubated at 37° C in a shaking incubator for 48 hrs.

At the termination of the incubation period, observations were made for cytotoxicity to the chorioallantoic membranes, and hemagglutination tests were made on each egg-bit culture of each dilution series.

Tissue damage was not observed except in the five wells receiving the highest concentration of the antimicrobial agent (=the 100 $\mu$g/ml). Tissues in all other treatments containing the antimicrobial agent appeared free of cytotoxic reaction as did all cultures in the control series.

No hemagglutination was observed in any of the wells of any series receiving the agent. However, virus was demonstrated in tissue culture wells in the control samples. All control wells at $10^{-3}$ and $10^{-4}$ titration dilutions gave positive hemagglutination reactions and one of the five wells in the $10^{-5}$ dilution series was positive. There was no hemagglutination reaction in the check series at $10^{-6}$ and $10^{-7}$ dilutions.

To ascertain whether the lack of hemagglutination in tissue cultures treated with the agent was due to an inactivation of the virus or simply due to tissue damage (lack of hemagglutination may merely have meant a lack of viral replication due to various causes) other tests were conducted.

The agent was used in place of antiserum in a virus neutralization test, starting with one-half the level of the agent found cytotoxic to egg-bits in tissue culture as ascertained in the previous test. Tenfold dilutions were assessed against $1 \times 10_2$ NDV egg-bit infection units/ml.

One-half ml of a 100 $\mu$g/ml concentration of the agent in tissue culture medium was placed in each of 8 egg-bit culture wells (series 1). One-half ml of 10 $\mu$g/ml concentration of the agent in tissue culture medium was placed in each of 8 egg-bit culture wells (series 2). One-half ml of 1 $\mu$g/ml concentration of the agent in tissue culture medium was placed in each of 8 egg-bit culture wells (series 3), etc. until 6 tenfold dilutions series of the agent in tissue culture medium had been prepared in eight replications. In a companion set of tenfold dilutions, non-immune serum diluted with tissue culture medium was used in six replications. In another companion set of tenfold dilutions, NDV antiserum diluted with tissue culture medium was used in two replications.

To each well of every treatment, 0.5 ml of NdV suspension containing $1 \times 10^4$ egg-bit infection units per ml was added, mixed and incubated for 30 min. at room temperature. After the incubation period, egg-bit tissue culture pieces were added to each well aseptically and treatments were incubated for 48 hrs. at 37° C.

At the end of the incubation period observations were made for cytotoxicity, and hemagglutination tests were made on all egg-bit cultures.

Results conclusively demonstrate that 5 μg antimicrobial agent per ml will effectively inhibit $1 \times 10^2$ eggbit infection units per ml from producing hemagglutinating virus in egg-bit culture. There was no evidence of cytotoxicity in any well.

The minimum inhibitory concentrations of the antimicrobial agent of this invention against an array of viruses, fungi and bacteria in appropriate culture media are listed below:

| Viruses | Minimal Inhibitory Concentration |
|---|---|
| Paramyxovirus - Newcastles Disease virus, (strains NJ-Roakin, Velogenic strain GB-Texas, and Blacksburg strain 4423) | 6 μg/ml |
| Rhabdovirus - Vesicular stomatitis virus (Indiana serotype) | 6 μg/ml |

-continued

| Viruses | Minimal Inhibitory Concentration |
|---|---|
| Leukovirus (RNA - Tumor Virus) - Rous Sarcoma Virus (Bryan high-titer strain) | 6 μg/ml |
| Poxvirus - Vaccinia virus (IHD strain) | 6 μg/ml |
| Herpesvirus - Herpes simplex (HF strain) - Mareks Disease strain | 6 μg/ml |

These viral entities are recognized as the agents of divers diseases of vertebrate animals. For example:

Newcastles disease virus causes a lethal neural and respiratory disease in fowls and is serologically closely related to human measles, canine distemper and rinderpest viruses.

Vesicular stomatitis virus causes infections in cattle and pigs clinically indistinguishable from Rhinovirus — Foot and mouth disease virus.

Rous sarcoma virus causes neoplastic disease in fowls.

Vaccinia virus causes cowpox disease in cattle and is immunologically equivalent to smallpox and monkey pox viruses.

Herpes simplex virus strains cause numerous diseases in vertebrates from cold sores and blindness in humans to cervical cancer. It causes blindness, malignancies and abortions in rabbits, cattle, and horses. The Marek's disease strain causes proliferative lesions in domestic poultry.

Table 2, hereinafter, lists the minimum inhibitory concentration of the antimicrobial agent of the invention against a wide variety of microorganisms.

Table 2

In vitro antifungal and antibacterial spectrum of antimicrobial invention

| Organism | Diseases Incited | Culture inhibition (% of control) in 48 hrs vs 1 week | | | | | |
|---|---|---|---|---|---|---|---|
| | | 1 μg/ml | | 10 μg/ml | | 100 μg/ml | |
| Fungi: | | | | | | | |
| Alternaria solani | Leaf molds of potato & tomato | 90 | 95 | 66 | 43 | 16 | 9 |
| Alternaria tenuis | Fruit rot of apples, grapes, vegtables | 70 | 80 | 25 | 20 | 16 | 15 |
| Alternaria tomato | Fruit rot of tomato | 90 | 100 | 27 | 44 | 27 | 44 |
| Alternaria zinniae | Seed rots of vegetables | 90 | 91 | 20 | 12 | 18 | 6 |
| Aphanomyces eutiches | Root rot of peas | 87 | 69 | 74 | 14 | 0 | 0 |
| Armillaria mellea | Root rot of all trees & shrubs | 67 | 51 | 0 | 0 | 0 | 0 |
| Ascochyta chrysanthemi | Flower blights | 99 | 100 | 39 | 19 | 29 | 10 |
| Ascochyta pisi | Leaf and pod spots of peas, beans, clover | 100 | 100 | 47 | 47 | 22 | 28 |
| Aspergillus flavus | Fruit and pod rots of peas & peanuts | 100 | 100 | 14 | 12 | 14 | 2 |
| Aspergillus niger | Storage rot of fruit & vegetables | 85 | 98 | 50 | 90 | 31 | 20 |
| Botrytis cinerea | Molds and rots of stored fruit & vegetables | 23 | 19 | 11 | 4 | 0 | 0 |
| Candida albicans | Digestive tract pathogen in fowls Clover root pathogen | 81 | 38 | 47 | 19 | 13 | 3 |
| Cephalosporium gramineum | Vascular wilt of wheat & cereals | 40 | 10 | 0 | 0 | 0 | 0 |
| Ceratocystis piceae | Wilt & rot of pines & firs | 95 | 99 | 89 | 80 | 77 | 54 |
| Ceratocystis fimbriata | Wilt & rot of hardwoods & sweet potatoes | 80 | 80 | 24 | 18 | 14 | 6 |
| Cercospora beticola | Leaf spot of beets & sugar beets | 98 | 100 | 54 | 66 | 22 | 31 |
| Cercosporella herpotrichoides | Root rot of cereals | 100 | 100 | 61 | 46 | 25 | 18 |
| Cladosporium cucumerinum | Scab of cucumbers | 100 | 84 | 20 | 20 | 0 | 0 |
| Cladosporium fulvum | Leaf mold of tomato | 100 | 77 | 32 | 14 | 0 | 0 |
| Cytospora cincta | Branch canker fruit trees | 100 | 100 | 82 | 71 | 29 | 13 |
| Endomyces malus | Apple storage rot | 90 | 70 | 0 | 2 | 0 | 0 |
| Erysiphe graminis (spores) | Mildew of cereals | 30 | 30 | 0 | 0 | 0 | 0 |
| Erysiphe polygoni (spores) | Mildew of legumes, beets, cabbage | 40 | 40 | 10 | 10 | 0 | 0 |
| Fomes pini | Wood rot of pines, firs | 90 | 80 | 15 | 15 | 0 | 0 |
| Fomes pinicola | Wood rot of pine, fir, spruce, hardwoods | 100 | 90 | 50 | 50 | 50 | 50 |
| Fusarium avenaceum | Rots of truck, fruit & nursery crops | 100 | 100 | 64 | 34 | 50 | 22 |
| Fusarium culmorum | Root rot of cereals & legumes | 98 | 81 | 74 | 34 | 33 | 28 |
| Fusarium nivale | Snow mold of turf | 74 | 12 | 0 | 0 | 0 | 0 |
| Fusarium oxysporum pisi Race 1 | Wilt of peas | 78 | 43 | 26 | 21 | 16 | 14 |
| Fusarium oxysporum pisi Race 2 | Wilt of peas | 62 | 28 | 10 | 6 | 0 | 0 |
| Fusarium oxysporum pisi Race 4 | Wilt of peas | 74 | 28 | 11 | 6 | 0 | 0 |

Table 2-continued

In vitro antifungal and antibacterial spectrum of antimicrobial invention

| Organism | Diseases Incited | Culture inhibition (% of control) in 48 hrs vs 1 week | | | | | |
|---|---|---|---|---|---|---|---|
| | | 1 μg/ml | | 10 μg/ml | | 100 μg/ml | |
| *Fusarium roseum sambucinum* | Root of storage rots of cabbage, cukes, beans & potatoes | 94 | 41 | 52 | 29 | 34 | 14 |
| *Fusarium solani eumartii* | Root & storage rot of potato | 87 | 42 | 50 | 21 | 44 | 21 |
| *Fusarium solani phaseoli* | Root rot of beans | 79 | 32 | 17 | 11 | 0 | 0 |
| *Fusarium solani pisi* | Root rot of peas | 64 | 42 | 14 | 10 | 8 | 2 |
| *Gelasinospora tetrasperma* | Root rot of beets | 88 | 97 | 17 | 47 | 12 | 24 |
| *Geotrichum candidum* | Pink stain of pine & oak, vegetable rots | 80 | 46 | 12 | 5 | 12 | 2 |
| *Glomerella cingulata* | Fruit & foliage rots & spots | 90 | 12 | 0 | 0 | 0 | 0 |
| *Guignardia vaccinii* | Fruit rot and blight of cranberry | 97 | 74 | 43 | 21 | 16 | 3 |
| *Helminthosporium sativum* | Root rot of Cereals; blight of corn | 83 | 80 | 26 | 14 | 23 | 12 |
| *Hypoxylon pruinatum* | Wood canker of hardwoods | 100 | 100 | 71 | 52 | 39 | 26 |
| *Neurospora crassa* | Bread, fruit & seed molds | 89 | 30 | 0 | 0 | 0 | 0 |
| *Penicillium expansum* | Storage rot of apples, pears, cherries | 93 | 84 | 32 | 11 | 15 | 4 |
| *Pholiota adiposa* | Wood rot of conifers & hardwoods | 84 | 37 | 0 | 0 | 0 | 0 |
| *Phomopsis vaccinii* | Rots & dieback of cranberries & azalea | 89 | 66 | 23 | 4 | 0 | 0 |
| *Phytophthora cinnamomi* | Root & collar rots of trees & shrubs | 100 | 100 | 35 | 60 | 17 | 54 |
| *Phytophthora crytogea* | Stem rot & wilts of annual flowers | 79 | 62 | 18 | 16 | 16 | 15 |
| *Phytophthora infestans* | Root & storage rots of potato & tomato | 100 | 100 | 100 | 82 | 84 | 71 |
| *Polyporus abietinus* | Wood rot of conifers | 66 | 53 | 0 | 0 | 0 | 0 |
| *Polyporus hirsutus* | Wood rot of conifers, hardwood, & shrubs | 90 | 91 | 25 | 20 | 12 | 10 |
| *Polyporus schweinitzii* | Wood rot of conifers & hardwoods | 80 | 62 | 20 | 4 | 0 | 0 |
| *Polyporus versicolor* | Wood rot of all woods | 100 | 93 | 17 | 18 | 8 | 14 |
| *Polyporus volvatus* | Wood rot of conifers | 100 | 95 | 66 | 50 | 48 | 32 |
| *Poria latemarginata* | Wood rot of hardwoods | 76 | 34 | 6 | 1 | 0 | 0 |
| *Pythium debaryanum* | Root rot of truck crops | 100 | 100 | 84 | 77 | 67 | 51 |
| *Pythium ultimum* | Root rot of vegetables | 100 | 92 | 51 | 47 | 49 | 48 |
| *Rhizoctonia solani* | Root rot of fruits & vegetables | 100 | 84 | 90 | 24 | 72 | 19 |
| *Schizophyllum commune* | Slash & sap rot of trees | 96 | 100 | 22 | 68 | 20 | 66 |
| *Sclerotinia fructicola* | Fruit rots of cherries, peaches, apples, pears | 63 | 11 | 0 | 0 | 0 | 0 |
| *Sclerotinia sclerotiorum* | Rots of most crops | 68 | 7 | 0 | 0 | 0 | 0 |
| *Sclerotium cepivorum* | Root rot of onion | 100 | 100 | 17 | 15 | 9 | 2 |
| *Septoria trifolii* | Blight of wheat | 100 | 79 | 57 | 37 | 18 | 4 |
| *Sphaerotheca pannosa* (spores) | Rose mildew | 100 | 100 | 32 | 32 | 0 | 0 |
| *Stemphyllium botryosum* | Seed rots of fruit & vegetables | 74 | 68 | 19 | 16 | 16 | 16 |
| *Suillus tomentosa* | Slash & wood rot of woody plants | 72 | 84 | 16 | 30 | 12 | 30 |
| *Thielaviopsis basicola* | Root & storage rot of carrots & legumes | 62 | 46 | 0 | 0 | 0 | 0 |
| *Tilletia caries* (spores) | Smut of wheat | 44 | 44 | 0 | 0 | 0 | 0 |
| *Trichoderma lignorum* | Wood stain of wood & seed rot of beans & peas | 81 | 72 | 21 | 3 | 0 | 0 |
| *Typhula idahoensis* | Snow mold of wheat | 44 | 37 | 0 | 0 | 0 | 0 |
| *Typhula incarnata* | Snow mold of wheat | 40 | 42 | 0 | 0 | 0 | 0 |
| *Urocystis colchici* (spores) | Smut of onion | 39 | 39 | 19 | 19 | 0 | 0 |
| *Uromyces phaseoli* (spores) | Bean rust | 41 | 41 | 2 | 2 | 0 | 0 |
| *Venturia inaequalis* | Apple scab | 89 | 69 | 20 | 7 | 0 | 0 |
| *Verticillium alboatrum* | Root rots & wilt of most plants | 100 | 87 | 33 | 11 | 15 | 8 |
| Bacteria: | | | | | | | |
| *Aerobacter aerogenes* | Root nodule Rhizobial of legumes | 87 | 87 | 39 | 14 | 0 | 0 |
| *Agrobacterium tumefaciens* | Crowngall of plants | 66 | 42 | 0 | 0 | 0 | 0 |
| *Bacillus megatherium* | Soft rot of potato | 98 | 98 | 89 | 44 | 72 | 27 |
| *Bacillus subtilis* | Soft rot of vegetables | 99 | 100 | 77 | 41 | 11 | 4 |
| *Corynebacterium flacumfaciens* | Bacterial wilt of beans | 99 | 89 | 89 | 82 | 49 | 17 |
| *Corynebacterium michiganese* | Bacterial canker of tomato | 79 | 82 | 67 | 29 | 17 | 11 |
| *Corynebacterium sepedonicum* | Ring rot of potatoes | 100 | 100 | 90 | 80 | 60 | 40 |
| *Escherichia coli* | Intestinal pathogen | 100 | 100 | 100 | 93 | 100 | 87 |
| *Klebsiella pneumonia* | Incitant of lobar pneumonia | 100 | 100 | 88 | 69 | 39 | 7 |
| *Proteus vulgaris* | Gastrointestinal disorders | 93 | 93 | 86 | 77 | 16 | 2 |
| *Pseudomonas lacrymans* | Bacterial spot of cucumber | 100 | 100 | 100 | 100 | 100 | 100 |
| *Pseudomonas syringae* | Bacterial canker of stone fruits | 100 | 100 | 100 | 100 | 100 | 100 |
| *Sarcina lutea* | Soil & air saprophyte | 26 | 7 | 0 | 0 | 0 | 0 |
| *Shigella dysenteriae* | Gastrointestinal disorders | 81 | 67 | 31 | 11 | 0 | 0 |
| *Staphylococcus aureus* | Skin infections, etc. | 64 | 38 | 22 | 9 | 0 | 0 |
| *Xanthomonas pelargonii* | Stem rot of geranium | 100 | 100 | 88 | 80 | 69 | 52 |
| *Xanthomonas vesicatoria* | Bacterial spot of tomato | 74 | 77 | 42 | 11 | 0 | 0 |
| Dermatophytes: | | | | | | | |
| *Microsporum gypseum* | Dermatophyte | 100 | 87 | 81 | 15 | 7 | 1 |
| *Trichophyton mentagrophytes* | Dermatophyte | 100 | 79 | 87 | 39 | 69 | 14 |

Minimum inhibitory concentrations were determined on the basis of a percent of check series as follows: 100% of check = no inhibition; 0% of check = total restriction of growth. Fungi were assessed on appropriate agar media in which 1 μg, 10 μg, or 100μ of antimicrobial agent was inmixed just prior to pouring plates. Fungi were transferred onto plates (5 replications at each concentration plus 5 checks), allowed to incubate at 25° C. for 48 hrs., and the average growth rates were determined and expressed in Table 2 as percent of check on the left hand side of the column. Five days later (7 days from the time of inoculation of plates) the comparative degree of inhibition was redetermined. These data are listed on the right hand side of the column.

Bacteria were evaluated in liquid shake culture, using a colorimeter to assess the relative inhibition of cell reproduction compared with the check series.

Various active derivatives of the products of this invention can be prepared, for example, pharmaceutically acceptable salts with acids and bases.

The products of this invention may be administered along but will generally be administered with pharmaceutically acceptable, non-toxic carriers, the proportions of which are determined by the suitability and chemical nature of the particular carrier, the chosen route of administration, and standard pharmaceutical practice. For example, in combatting various infections or in maintaining therapeutically effective levels in the blood or tissues, they may be administered orally in the form of tablets or capsules containing such excipients as starch, milk sugar, certain types of clay, etc. They may be enteric coated so as to be more resistant to the acid and digestive enzymes of the stomach. For parenteral administration they may be used in the form of a sterile solution containing other solutes, for example, enough saline or glucose to make the solution isotonic. A wide variety of dosage unit forms are possible.

The physician or veterinarian in attendance will determine the dosage regimen which will be effective. This will depend upon such factors as the age and weight of the patient, the degree and locus of the infection and the dosage unit form selected. Dosage unit forms containing from 25 to 250 mg are useful.

For treatment and control of plant diseases the products will often be suspended in an inert liquid, such as a hydrocarbon or halogenated hydrocarbon. Alternatively, they may be dissolved in a solvent. They may be dispersed in a dry carrier such as talc or various forms of clay. For plant use, the concentration will normally be at least 0.01% by weight based on the total weight and may be as high as 10% to 15% by weight. However, appreciable variations are possible. The compositions may also be provided as concentrates to be diluted with an appropriate inert carrier just prior to use.

Chickens and rabbits have been treated with products of this invention orally, parenterally and topically to control Newcastle disease and keratitis. Bean, tomato, wheat, barley, maize, zinnia, pea, lentil, soybean, tobacco, and lettuce seed have been dusted and soaked with products of this invention to control divers seed-borne plant pathogenic organisms. Tomato, potato, bean and cereal plants have been drenched as seedlings or stecklings to control plant pathogenic organisms. Levels as high as 0.1% have been used directly on seeds and plants of the species listed above without evidence of toxicity.

The following non-limiting examples are given by way of illustration only.

EXAMPLE I

Preparation of Tablets 1000 g of antimicrobial agent and 2000 g of lactose are thoroughly mixed together and the whole are passed through a 30 mesh sieve.

A paste is separately prepared with 80 g of cornstarch and 350 ml of distilled water.

The above mixture is well kneaded with the paste and the mass is passed through a 4 mesh sieve. The resulting globules are dried at 50° C for 15 hours.

The dried globules are then granulated first on a granulating machine and passed through a 16 mesh sieve. The grains are covered with a powdery mixture prepared by blending 30 g of calcium stearate, 200 g of cornstarch and 80 g of talc, and passed through a 40 mesh sieve.

Tablets each containing 50 mg of antimicrobial agent are made of the above-obtained granules in accordance with the conventional procedure known in the art.

EXAMPLE II

Preparation of Injection 100 g of antimicrobial agent are taken up in a quantity of distilled water specifically prepared for this purpose and made up to 5 liters. The mixture is made isotonic with addition of a predetermined amount of an aqueous solution of physiological salt.

Each 5 ml fraction of the mixture is filled in ampoules and sealed. The ampoules are sterilized at 121° C for 25 minutes in an autoclave at 15 lbs/in$^2$, followed by immediate dipping in a cold water bath.

EXAMPLE III

Preparation of an Aqueous Mixture for Oral Administration

A mixture consisting of:

| | |
|---|---|
| Antimicrobial agent | 35.0 g |
| Cane sugar | 100.0 g |
| Glycerine | 100.0 ml |
| Ethyl p-oxybenzoate | 1.5 g |
| Artificial orange essence | 0.2 ml |
| Essential oil of orange | 1.0 ml | is added to distilled water to make up 1000 ml of the final volume.

EXAMPLE IV

Preparation of Compositions for Plant Treatment

A. To a mixture containing 100 g of pulverized calcium carbonate, 2 g of olein and 1 g slaked lime is added 1.5 g of antimicrobial agent and the mixture is ground in a ball mill. The resulting powder is easily scattered and has good adhesive power.

B. A mixture of 5 mg of antimicrobial agent, 25 g of talcum, 4 g of sodium dibutyl naphthalene sulfonate, 4 g of casein and 5 g of sodium carbonate is ground in a ball mill. The mixture is added to an equal quantity of ground calcium carbonate and the whole thoroughly mixed. This powder may be suspended in water immediately before use. It provides a suspension which is sufficiently stable for use in spraying applications.

C. A solution is prepared containing 1 g of antimicrobial agent in 100 g of carbon tetrachloride. The mixture is useful in the treatment of infected plants by spraying.

D. A mixture is prepared containing 50 mg of antimicrobial agent, 20 g of xylene and 80 g of Turkey-red oil. This mixture can be readily emulsified in water and the resulting emulsion is suitable as a plant spray.

E. A suspension of 100 g of finely ground calcium carbonate in a solution containing 2 g of antimicrobial agent in methyl ethyl ketone is prepared and the ketone evaporated in vacuo. The resulting powder is easily sprayed to control fungi infections of plants.

What is claimed is:

1. An antimicrobial agent containing peptide, fatty acid and carbohydrate moieties, the peptide moiety containing:

| | |
|---|---|
| d-threonine | l-valine |
| d-alanine | l-serine |
| alloisoleucine | l-proline |
| d-valine | glycine |
| l-dehydrobutyrin | l-leucine |
| N-methyl threonine | l-isoleucine | the fatty acid moiety containing an analog of myristic acid unsaturated between carbon atoms 6 and 7, isotrideconoic acid, lauric acid and undecanoic acid; testing as follows in standard tests:

Molisch test — positive
Ninhydrin test — positive
Biuret test — positive
Anthrone test — negative
Carbazole test — weak positive
Tauber's test — negative
Benzidine-glacial HAC — negative
Bial's test — negative
Moore's test — negative
Lieberman-Burchard test -- negative having a molecular weight of about 14,000 being soluble in methyl ethyl ketone and insoluble in water and the infrared curve of FIG. 1, and the pharmaceutically acceptable salts thereof.

2. A therapeutic composition containing an antimicrobial agent of claim 1 as the principal active ingredient together with a pharmaceutically acceptable carrier.

3. A therapeutic composition of claim 2 in dosage unit form.

4. A method of treating viral infections in animal hosts which comprises administering a therapeutically effective quantity of an antimicrobial agent of claim 1 to an infected host.

5. A composition for the treatment or control of plant diseases comprising an antimicrobial agent of claim 1 in an inert carrier.

6. A composition of claim 5 containing from 0.01% to 15% by weight of the antimicrobial agent.

7. A method of treating viral plant infections which comprises administering a composition of claim 6 to a plant having a viral infection.

* * * * *